(12) United States Patent
Vines

(10) Patent No.: US 6,314,960 B1
(45) Date of Patent: Nov. 13, 2001

(54) DENTAL MEDICATION VACUUM PUMP DELIVERY TRAY

(76) Inventor: Frank L. Vines, 607 Columbiana Rd., Homewood, AL (US) 35209

( * ) Notice: Subject to any disclaimer, the term of this patent is extended or adjusted under 35 U.S.C. 154(b) by 0 days.

(21) Appl. No.: 09/162,329

(22) Filed: Sep. 28, 1998

(51) Int. Cl.[7] ........................................ A61C 5/14
(52) U.S. Cl. ............................. 128/859; 128/861
(58) Field of Search ........................ 128/846, 848, 128/859–862; 433/6, 215, 216, 217.1

(56) References Cited

U.S. PATENT DOCUMENTS 3,527,219 * 9/1970 Greenberg .......................... 128/861
3,536,069 * 10/1970 Gores .................................. 128/861
4,138,814 * 2/1979 Weitzman ........................... 128/861
5,682,904 * 11/1997 Stinnett .............................. 128/861

* cited by examiner

Primary Examiner—Michael A. Brown
(74) Attorney, Agent, or Firm—Thad G. Long

(57) ABSTRACT

A method and apparatus for delivery of medicaments to oral tissues is provided. The apparatus operates on the principle of a vacuum pump such that medicaments are essentially sucked into spaces within the dental tissue upon reversal of pressure from negative to positive pressure. The apparatus comprises a resilient plastic material forming a frontal buccal shield, and dental trays for upper and lower dental arches. The device is operated by moving the jaw in a chewing motion after placing medicaments in the upper and lower trays.

13 Claims, 4 Drawing Sheets

DENTAL MEDICATION VACUUM PUMP DELIVERY TRAY

FIELD OF THE INVENTION

This invention relates to methods and devices for administration of medicaments to oral tissues. More specifically, this invention relates to devices and methods of treatment of diseases of the teeth and gums.

BACKGROUND OF THE INVENTION

Fossil evidence indicates that periodontal disease and dental caries have plagued mankind throughout the history of human existence. Both dental caries and periodontal disease are caused by the bacterial invasion and colonization of the dental plaque, which invasion is constantly in progress on all tooth surfaces exposed within the oral cavity.

Sampling and identification of the plaque bacteria indicate that a wide variety of bacteria coexist as infective agents within the dental plaque. To date, it has not been possible to identify any one organism as the singular pathogenic agent in either dental caries or periodontal disease. It is probable that several infective organisms interact synergistically to cause such diseases.

Throughout history, the mechanical removal of bacteria-laden dental plaque from the teeth on a daily basis has been the first line of defense against dental caries and periodontal disease. However, mechanical methods to remove plaque, such as by brushing, are not effective in removing such plaque from a significant portion of dentition surface area. Moreover, because plaque bacteria reproduce rapidly, recolonization of such mechanically cleaned areas occurs within twenty-four hours.

The extent to which oral disease agents can be kept in check is dependent on several factors which are, in order of importance, (i) daily mechanical removal, (ii) the individual's immune competence, (iii) regularity of dental check-ups and cleaning, and (iv) use of intraoral chemical plaque control agents such as rinses and toothpastes. The current invention is primarily designed to affect factors (i) and (iv).

Currently several methodologies are utilized to control dental caries and periodontal disease. Some methodologies comprise rinses which are only partially effective in killing plaque bacteria. Importantly, no rinse method will reach the subgingival plaque which is of greatest threat to dental health.

Other methodologies utilize systemic antibiotics. Delivery of antibiotics via the bloodstream is reasonably effective in controlling gingival infections where the plaque bacteria have invaded the tissues adjacent to the plaque. However, systemic antibiotics have very limited capability to kill plaque bacteria which reside within the plaque itself, since the dental plaque has no blood supply.

In another example, polymeric compositions are disclosed which are designed to release medicament after implantation (U.S. Pat. No. 5,607,686). Such compositions must be carefully placed so as not to incite the formation of tissue adhesions. In yet another example, U.S. Pat. No. 4,681,544 discloses a device designed to retain an oral pack. Such device is semi-permanently mounted to the tooth and its only function is to retain the pack in place. The examples of these patents provide only localized administration of treatments. Various mouth devices for inhibiting snoring and sleep apnea, such as U.S. Pat. Nos. 5,056,534, 5,365,945, 5,003,994, 5,042,506, 3,434,470, 4,304,227, 4,676,240, 5,092,346, 5,117,816, 5,277,202 and others. None of these have been applied against periodontal disease.

Thus, regardless of typical methods utilized to treat and prevent dental disease, it has been all but impossible to effectuate fully the elimination of anything close to 100% of such disease causing agents. In contrast to devices and methodologies which rely on rinses or systemic administration, the current invention provides a novel technique and device which will cause the administration of medicaments into the dental plaque by mechanical action comprising chewing motions of the jaw combined with an apparatus designed to act as an alternating high pressure/low pressure pump.

SUMMARY OF THE INVENTION

The object of this invention is to deliver medication to the teeth and gums of a human. More particularly, it is the object of this invention to deliver medication to the root surfaces of the teeth and gingival tissues within the gingival crevices below the gum line, where it has traditionally been difficult to deliver medication effectively. It is a further object of the invention to deliver medication to the farthest reaches of any periodontal pockets existing under the gums.

One embodiment of the invention provides for a resilient buccal shield across the front of the device which acts to seal the mouth cavity from air flow around the lips.

Another embodiment of the invention provides for resilient upper and/or lower dental arch receiving trays wherein the trays are made so as to encompass all the teeth of the upper and/or lower arches. A further embodiment of the invention provides medication reservoirs or pockets within the trays that further provide action as a rubber-bulb type suction pump.

It is another object of the invention to deliver medicament to oral tissues by succession of positive and negative pressures created from the alternating formation of a partial vacuum and release thereof in and around the gingival tissues. It is a further embodiment for the partial vacuum to be created by action of up and down jaw movement in relation to dental arch receiving trays of the invention.

DETAILED DESCRIPTION OF THE INVENTION

Figure 1:
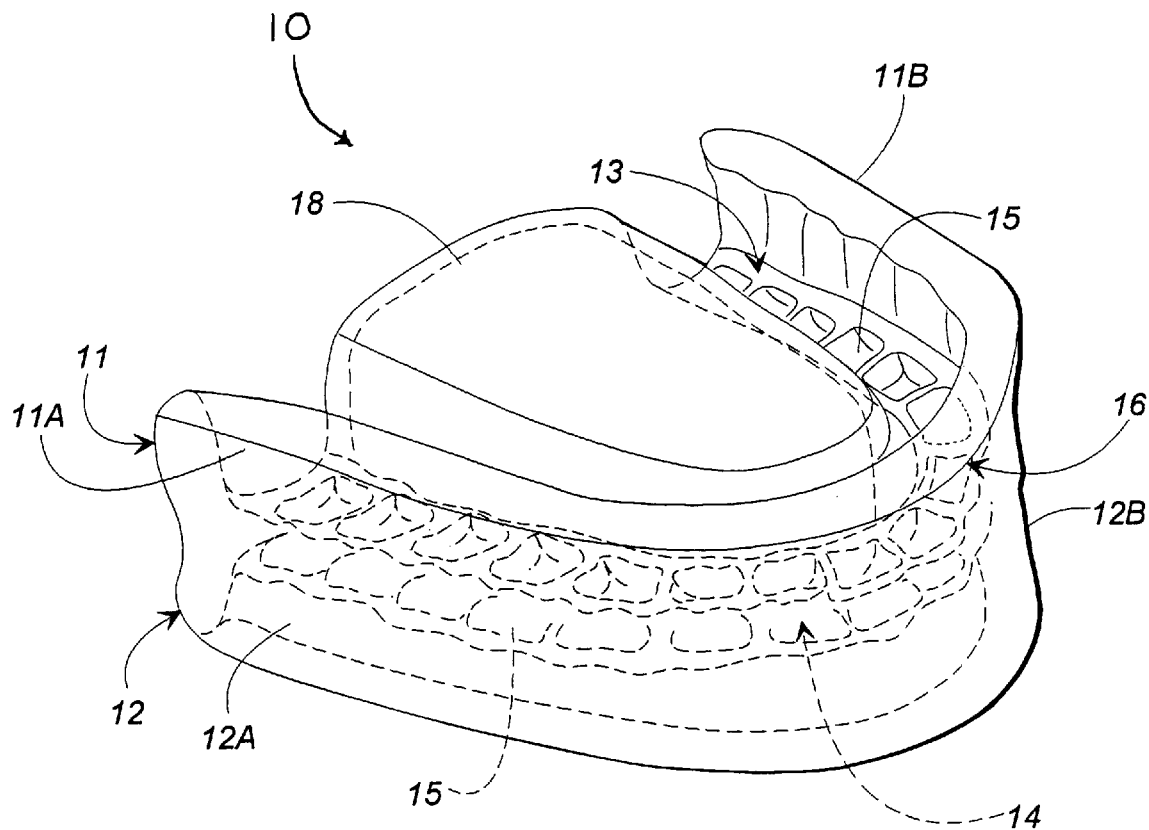
FIG. 1 is a perspective view of the device seen from above and in front thereof.

Turning to FIG. 1, a device 10 made of a resilient material such as ethyl vinyl acetate is disclosed. Proper placement of the device within the mouth will cause the teeth of the upper and lower arches to rest within the upper and lower dental trays 11, and 12 respectively. The floor 13 of the upper tray 11 and ceiling 14 of the lower tray 12 provide enough space for the volume of the teeth plus a small excess which excess space may be provided in the form of pockets 15. The pockets provide a dual function wherein one function is to provide space for a generally fluid, paste, gel, or small granule medication, and a second function is to provide air space which may be compressed to create positive pressure or vacated to form a partial vacuum. Of course, the device would work with a single tray at the top or at the bottom, or even on certain target teeth less than the entire upper and lower plates, but generally it would be prudent to treat all teeth.

The front of the device 10 provides a buccal shield 16 covering both the upper and lower dental trays. Additionally, the buccal shield 16 is integrally connected to the outer lateral sides 11A and 12A of the dental trays, i.e., upper outer side of tray 11, and lower outer side of tray 12. The upper and lower trays extend rearward so as to encompass the rearward most tooth of the left and right upper and left and right lower arches respectively.

The dental trays further provide lower inner side 12B and upper inner side 11B. Integral to the upper arch left and right inner sides is optionally connected a palate plate 18 (see FIG. 7).

Figure 2:
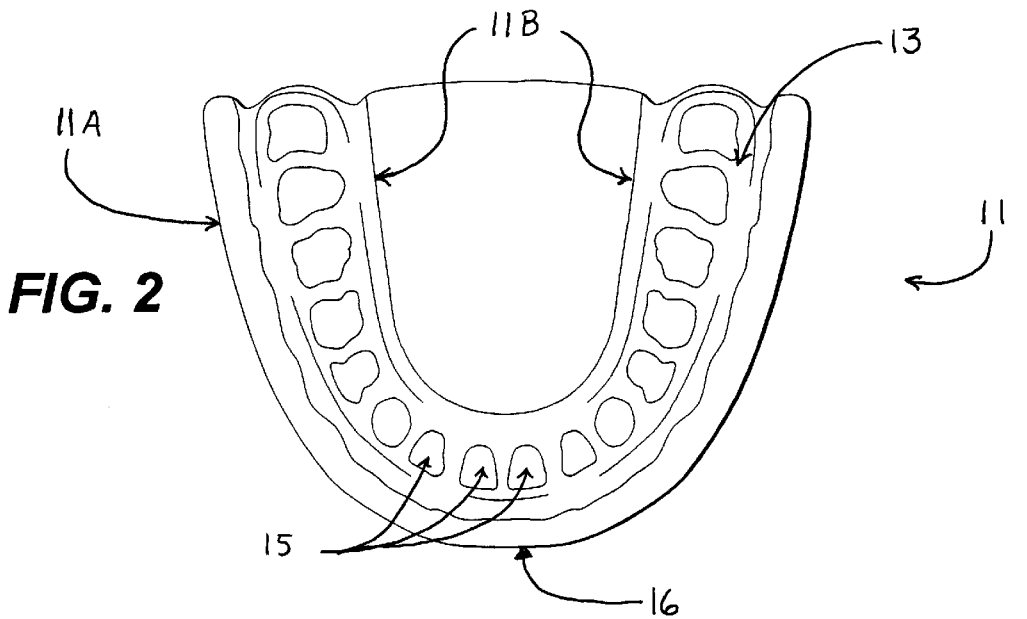
FIG. 2 is a perspective view from directly above the device.

FIG. 2 shows the upper tray 11, with the tops of outer sides 11A and inner sides 11B visible, between which sides at the floor 13 there are pockets 15 designed to receive individual upper teeth of a person. The upper portion to the buccal shield 16 is also indicated on FIG. 2. Not shown but extending directly below the configuration in FIG. 2 would be a corresponding lower tray, with similar corresponding individual features, which lower tray is designed to receive the lower teeth of a person. Thus, when the device 10 is inserted into the mouth, the teeth will fit into upper and lower trays 11 and 12 and comfortably into pockets 15 and 17 at the respective floor 13 and ceiling 14 of said trays with a buccal shield 16 connecting the trays in front so as to enable the wearer of the device to block the intake of air through the mouth. This will be an important attribute of this device and its utilization, as will be described in more detail hereafter.

Figure 3:
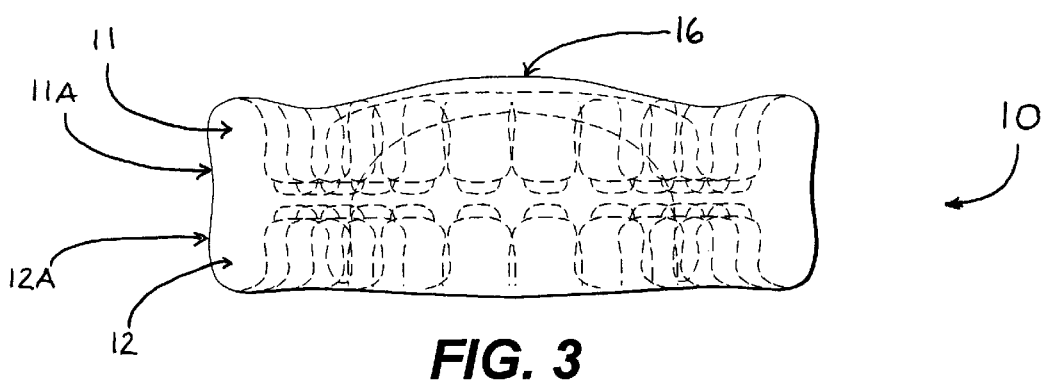
FIG. 3 is a frontal view of the device.

FIG. 3 shows the device 10 from the front, depicting upper tray 11 and lower tray 12 molded together as integral parts of a single device, with outer side 11A of the upper tray 11 visible, and outer side 12A of the lower tray 12 also visible. The entire outward facing portions of the device 10 effectively form a shield to aid against the intake of air through the mouth, but the most critical portion thereof is the front portion where air is most likely to enter the mouth, and this front portion has been designated as the primary buccal shield 16 for the purpose of the descriptions included herein.

Figure 4:
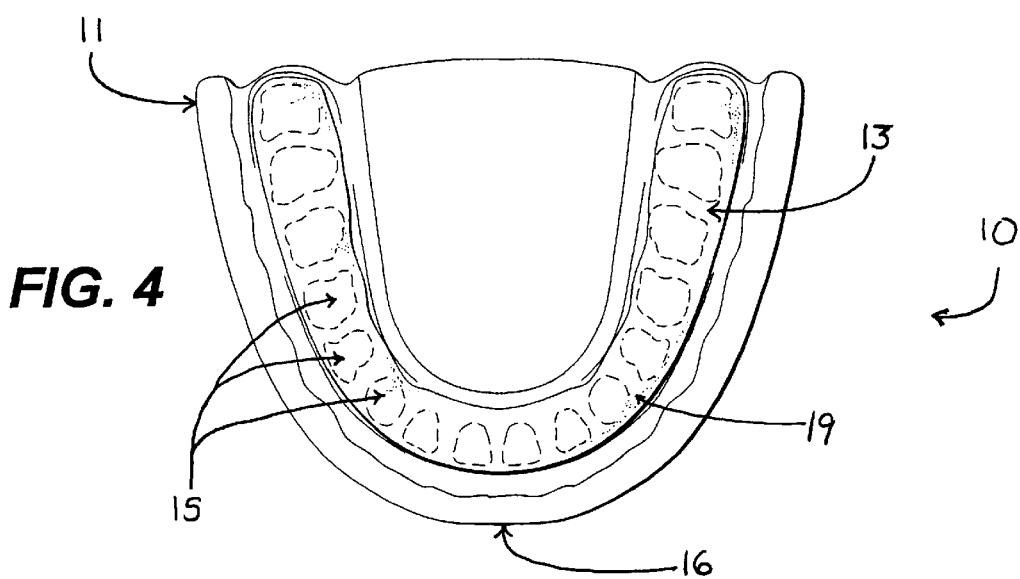
FIG. 4 is a perspective view of the device as seen from above, with medicament placed within the upper tray thereof.

In operation, as illustrated in FIG. 4, medicament is placed in the floor 13 of the upper tray 11 and ceiling 14 of the lower tray 12, not shown, and then the device is placed in the mouth such that the teeth of the upper and lower arches are within the said upper and lower dental trays. The medicament 19 substantially fills the pockets 15 within the floor 13 (and the pockets 17 of the ceiling 14, not shown). Next, the user must create a partial vacuum by the acts of swallowing and then allowing the lower jaw to drop somewhat to the normal rest position of the mandible with the lips sealed. This normal physiologic intra-oral vacuum formation occurs unnoticed every time a person swallows. One can accentuate and dramatically demonstrate this vacuum formation by swallowing and then, while keeping the lips sealed, drop the mandible approximately an inch or more. The cheeks and lips will be drawn in between the teeth with the vacuum formed. From a pure physics point of view the partial vacuum is formed by the increase of the intra-oral volume with the oral and naso-pharyngeal entrances to the oral cavity sealed. Thus, in the absence of the device within the mouth, there is the natural tendency of the cheeks to be sucked inward as the jaw is lowered, thereby relieving some of the potential for the creation of a partial vacuum within the mouth. However, the presence of the device 10 will keep the cheeks from moving inward. Moreover, the frontal buccal shield 16 will provide a dam such that even if the lips are not able to be kept closed, passage of air out of the mouth will still be blocked.

Figure 5:
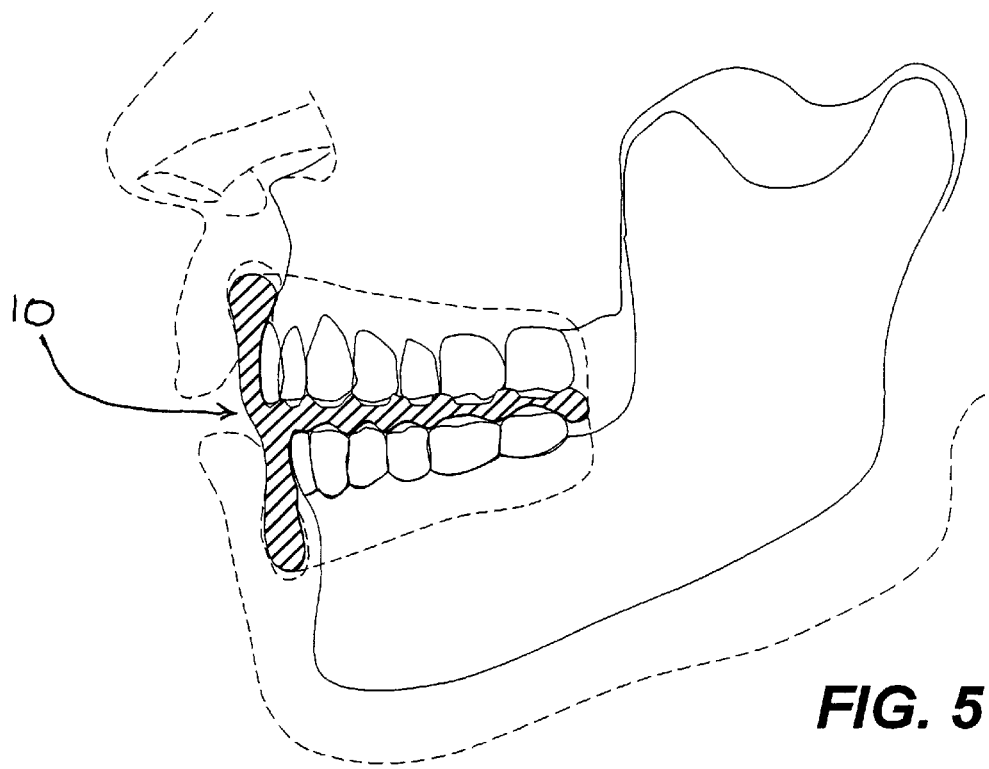
FIG. 5 is a cross-sectional perspective diagrammatic view of the naso-pharyngeal portion of a human head seen from the left side thereof showing the device inserted over the upper and lower teeth within the mouth in position to be utilized for the intended purposes.

FIG. 5 illustrates diagrammatically the left side of a person's naso-pharyngeal area, showing the device 10 in place around the upper and lower teeth as described above.

Because the cheeks cannot fold inward to reduce the volume of the intraoral cavity due to the presence of the device's outer dental tray walls, the partial vacuum formed becomes measurably strong. The maximum strength of the vacuum formed will be limited only by the strength of the submandibular jaw opening muscles and the height of contour of the frontal buccal shield and dental tray outer walls.

Figure 6:
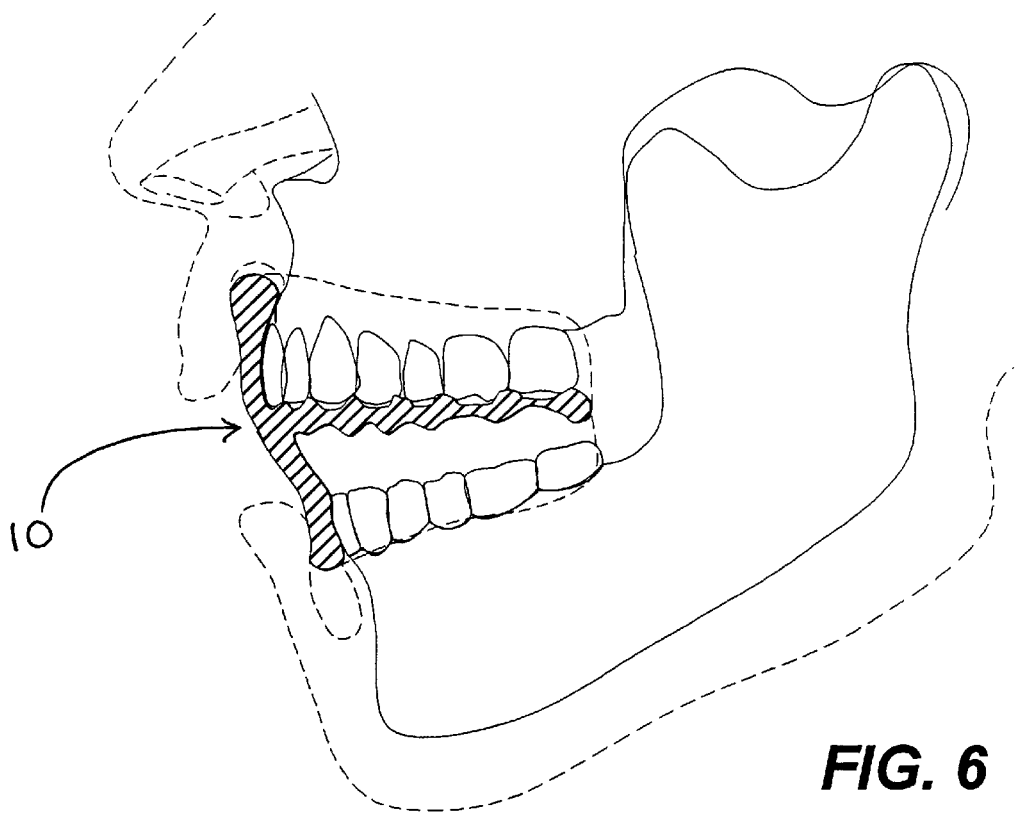
FIG. 6 is a cross-sectional view similar to that of diagrammatic FIG. 5 except that the jaw of the human has dropped as a part of the series of motions utilizing the device.

FIG. 6 illustrates the jaw or mandible slightly dropped. As the jaw is dropped, the buccal shield slides out from under the buccal pouch on the maxilla and out from under the buccal pouch of the mandible. The dropping of the jaw causes the intra-oral volume progressively to increase to the point of doubling the intra-oral volume in most persons before the edges of the buccal shield reach the lip line. When either the edge of the buccal shield extending over the maxilla and mandible reaches the lip line, the oral seal is broken, and the pressure within the oral cavity is equalized with the outside pressure.

Figure 7:
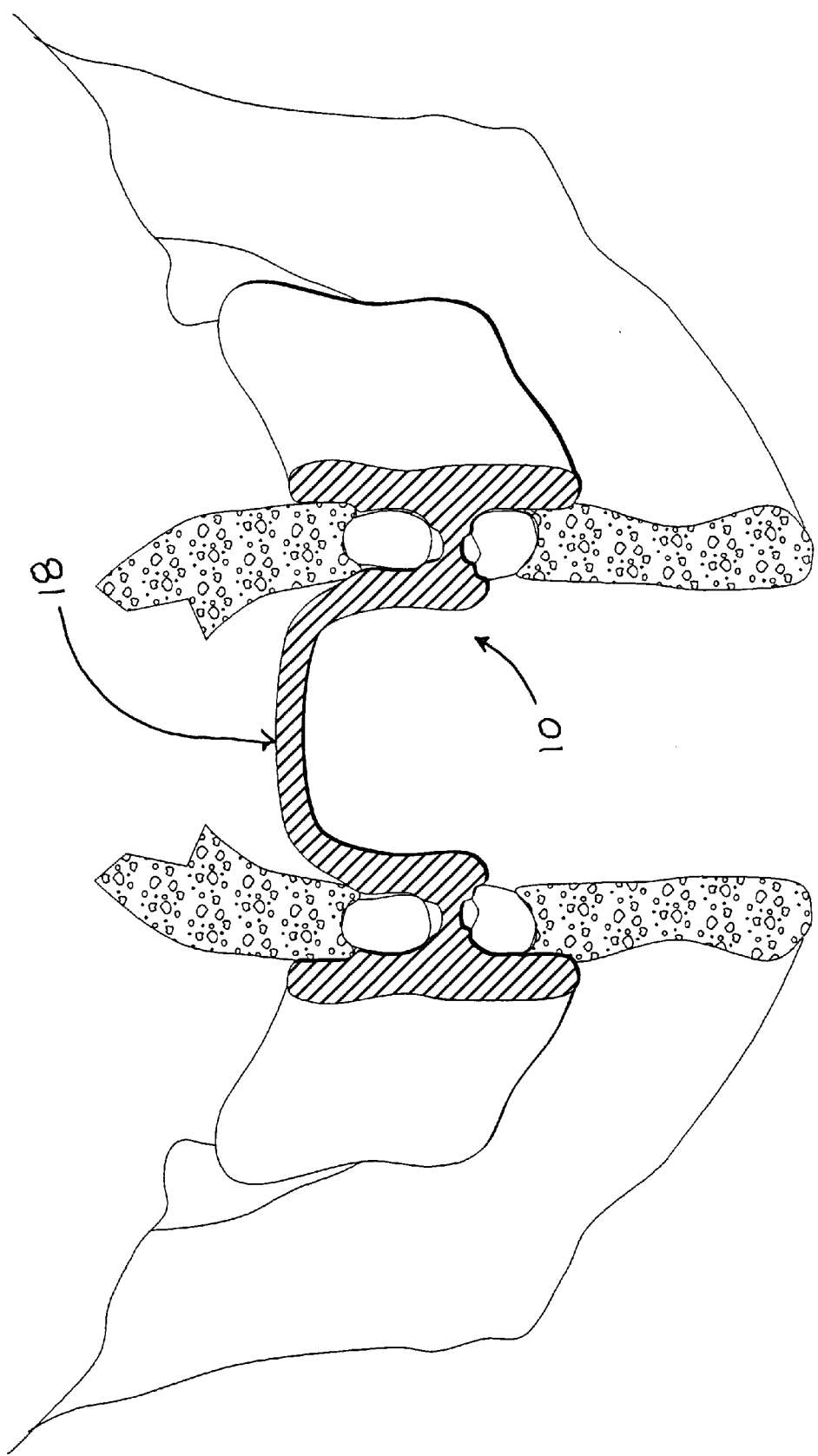
FIG. 7 is a cross-sectional diagrammatic view of the pharyngal portion of a human head as seen from the front, showing the device in place over the teeth (no tongue shown).

FIG. 7 shows the mouth diagrammatically viewed from the front with the device 10 in place. The palate plate 18 is shown spanning the palate of the mouth.

The partial vacuum that can be created by slight downward displacement of the jaw is near several ounces per square inch. A greater vacuum can be created by the user's forcibly dropping the mandible to a maximal position without losing the partial vacuum. Such vacuum increase is caused by the considerable increase in the intraoral volume and can give rise to a partial vacuum in the order of several pounds per square inch.

Movement of the jaw to create a partial vacuum within the oral cavity further results in the sides of the dental trays closing in on the teeth and gums due to the negative pressure within the medication pockets. The resilient material of the device will deform such that the teeth and gums come into close mechanical contact with the walls of the dental trays and the medication pockets.

To review the mechanism of action, the molded pliable shield that arches horizontally from the second or third molar area on one side of the user's dental tray all the way around to the second or third molar area on the other side of the user's dental tray, and further extends vertically to the height and depth of the upper and lower buccal pouches, is the key element in creating the intraoral partial vacuum as the user lowers the jaw. The dental tray areas form a secondary partial vacuum chamber enclosing the teeth and gums. The lingual aspect of this molding on the lower arch extends vertically down to the tissue reflection line, or floor of the mouth, all the way around the arch. The lingual aspect of the molding on the upper arch covers the teeth and gums and palate from one side of the arch to the other side. As the mandible begins to drop, a partial vacuum is created within the oral cavity. The partial vacuum created further effects low pressure environment in the secondary chamber via leaks of air from the medication pockets under the edges of the dental trays. As the partial vacuum becomes established within the secondary chamber, the edges of the dental tray walls suck down into intimate contact with the oral tissues all the way around the upper and lower arches.

At the point of maximum vacuum the medication pockets within the secondary chamber bulge over the occluding surfaces of the teeth and are filled with medication. Upon releasing the partial vacuum or negative pressure, by raising the jaw to its closed position, medication is caused to be pushed into intimate contact with gingival tissues. Moreover, closing the jaw with strong biting pressure activates the "rubber bulb" function of the medication pockets and acts to force medication matter into periodontal pockets and hard-to-reach crevices. Essentially, the device properly manipulated acts as an extremely effective negative/positive pressure pump as the negative pressure within the medication trays becomes extreme when the intra-oral volume approaches double its prior size. With the lowering of the mandible, the softer portions of the bacteria-laden dental plaque are sucked from the interdental spaces, subgingival crevice and periodontal pockets, and are forced into contact with the medication. As the teeth are then clenched, the medication is forced into periodontal pockets, interdental crevices, and normal gingival crevices. The repetition of this sequence of clenching of the teeth and then dropping the mandible to a point short of losing the intraoral partial vacuum actually makes this appliance a very effective vacuum pump. Medication is delivered all the way into the interdental crevices, the normal gingival crevices, and the bottom of periodontal pockets. The device further aids in the mechanical removal of dental plaque from the surfaces of the teeth that it contacts by its frictional scraping over the contacted tooth surfaces.

After two weeks of once-a-day use with appropriate medications, the device has been proven to reduce gingival swelling, gingival inflammation, and root surface sensitivity. The device further positively affects the equilibrium between active and progressive periodontal disease and caries and inactive and controlled disease processes by delivering plaque and caries control medications to previously inaccessible portions of the dentition. For example, use of a 1½ percent formulation of hydrogen peroxide gel in the medication pockets virtually wipes out the entire group of anaerobic bacterial pathogens from the dental plaque.

The invention now being fully described, it will be apparent to one of ordinary skill in the art that many changes and modifications can be made thereto without departing from the spirit or scope of the appended claims. For example, dental arch trays for upper teeth only or for lower teeth only could be utilized, provided the upper or lower teeth can move in the trays relative to the trays, which can be accomplished by fixing the position of the respective trays relative to movement of the teeth. Also, while performance may be improved with dental trays custom-designed for the teeth of an individual patient, varying degrees of effectiveness may be achieved by means of dental trays not so custom-designed, as long as the medicament can be administered via dental trays in an environment of successive partial vacuums and release thereof, achieving the oral pump action described above.

I claim:

1. A method of delivering medicament to oral areas harboring dental plaque comprising the steps of:
   (a) placing a medicament into a dental arch tray;
   (b) placing the dental arch tray in contact with teeth of a user;
   (c) causing the creation of a partial vacuum extending within said dental arch tray and between said tray and said teeth;
   (d) reducing said partial vacuum of (c); and
   (e) causing the creation of positive pressure between said dental arch tray and said teeth.

2. A method of delivering medicament to oral areas harboring dental plaque as described in claim 1, wherein said medicament is in the form of a fluid, paste, gel or small granules.

3. A method of delivering medicament to oral areas harboring dental plaque as described in claim 1, wherein steps (c), (d) and (e) of claim 1 are repeated at least once after the sequence of steps (a) through (e) of claim 1.

4. A method of delivering medicament to oral areas harboring dental plaque as described in claim 2, wherein steps (c), (d) and (e) of claim 1, as incorporated in claim 2, are repeated at least once after the sequence of steps (a) through (e) of claim 1.

5. A device for delivering medicament to oral areas harboring dental plaque comprising:
   (a) a dental tray for receiving at least one tooth of a user, in which the medicament can be placed;
   (b) a shield means for facilitating an intraoral partial vacuum, preventing passage of air into the oral cavity through the mouth of said user for a normal range of open and closed positions of said user's lips; and
   (c) a means for retaining said tray in a substantially fixed position while allowing said user's tooth to move up and down in said tray.

6. A device for delivering medicament to oral areas harboring dental plaque as described in claim 5, wherein said shield means is a buccal shield integrally connected to a front portion of said dental tray.

7. A device for delivering medicament to oral areas harboring dental plaque as described in claim 6, wherein said means for retaining said tray in a substantially fixed position is the joinder of said dental tray to said buccal shield.

8. A device for delivering medicament to oral areas harboring dental plaque as described in claim 6, wherein said means for retaining said tray in a substantially fixed position is a palate plate.

9. A device for delivering medicament to oral areas harboring dental plaque as described in claim 6, wherein said means for retaining said tray in a substantially fixed position is the combination effect of (i) joinder of said dental tray to said buccal shield and (ii) a palate plate.

10. A device for delivering medicament to oral areas harboring dental plaque comprising:
   a) upper and lower dental trays for respectively receiving upper and lower dental arches of a user, said trays having outer and inner side walls, said outer side walls of said upper tray extending substantially to the height of the buccal pouches of a user when said user's teeth fully engage said upper tray, said inner side walls of said upper tray extending across said upper dental arch to the distal side so as to form a membrane to cover the palate of a user when in use, said outer side walls of said lower tray extending substantially to the depth of the buccal pouches of a user when said user's teeth fully engage said lower tray, said inner side walls of said lower tray extending substantially to the floor of the mouth of a user when in use;

b) a buccal shield integrally connected to a front portion of said upper and lower dental trays, facilitating an intraoral partial vacuum, said shield having a size and dimension capable of sealing off air flow from or into the mouth of a user when in use; and c) pockets for receiving medicament along inner surfaces of said upper and lower dental trays.

11. A device for delivering medicament to oral areas harboring dental plaque comprising:

a) an upper dental tray having outer and inner side walls, said outer side walls of said upper tray extending to the height of the buccal pouches of a user when said user's upper teeth fully engage said upper tray, said inner side walls of said upper tray extending across said upper dental arch to the distal side so as to form a membrane which will cover the palate of a user when in use, b) a buccal shield integrally connected to a front portion of said upper dental tray, facilitating an intraoral partial vacuum, said shield having a size and dimension capable of sealing off air flow from or into the mouth of a user when in use; and c) pockets for receiving medicament along an inner surface of said upper dental trays.

12. A device for delivering medicament to oral areas harboring dental plaque comprising:

a) a lower dental tray having outer and inner side walls, said outer side walls of said lower tray extending to the depth of the buccal pouches of a user when said user's lower teeth fully engage said lower tray, said inner side walls of said lower tray extending across said lower dental arch to the distal side and extending lingually to the floor of the user's mouth;

b) a buccal shield integrally connected to a front portion of said lower dental tray, facilitating an intraoral partial vacuum, said shield having a size and dimension capable of sealing off air flow from or into the mouth of a user when in use; and c) pockets for receiving medicament along an inner surface of said lower dental trays.

13. A device according to claim 2, 3, 4, 5, 10, 11 or 12 made of a resilient material selected from the group consisting of ethylene vinyl acetate copolymer and other resilient plastics.

* * * * *